United States Patent [19]

de Ruiter

[11] Patent Number: Plant 7,414

[45] Date of Patent: Jan. 8, 1991

[54] MINIATURE ROSE PLANT NAMED RUIFARO

[75] Inventor: Gijsbert de Ruiter, Hazerswoude, Netherlands

[73] Assignee: De Ruiter's Nieuwe Rozen B.V., Hazerswoude, Netherlands

[21] Appl. No.: 392,579

[22] Filed: Aug. 11, 1989

[51] Int. Cl.[5] ..... A01H 5/00

[52] U.S. Cl. ..... Plt./9

[58] Field of Search ..... Plt. 9

*Primary Examiner*—James R. Feyrer

*Attorney, Agent, or Firm*—Christie, Parker & Hale

[57] ABSTRACT

A new variety of miniature rose having medium pink flowers produced on a good pot forcing plant also suitable for growing outdoor in gardens.

2 Drawing Sheets

SUMMARY OF THE INVENTION

The present invention relates to a new and distinct variety of rose plant of the miniature rose class which was originated by my crossing two unnamed, unpatented seedlings of my creation. The varietal denomination of the new variety is "Ruifaro".

Among the novel characteristics possessed by this new variety which distinguish it from its parent and all other varieties of which I am aware are its attractive medium pink flowers borne on a plant suitable for production of flowering pot plants and as garden plants to be grown outdoor. "Ruifaro" can be reproduced through propagation by cuttings, budding or grafting. Flowers of the new variety are long lasting on the plant. Asexual reproduction by budding, grafting and from cuttings of the new variety as performed in Hazerswoude, Holland, shows that the foregoing and other distinguishing characteristics come true to form and are established and transmitted through succeeding propagation.

The accompanying drawings show typical specimens of the vegetative growth and flowers of the new variety in different stages of development and depicted in color as nearly true as it is reasonably possible to make the same in a color illustration of this character.

BRIEF DESCRIPTION OF THE DRAWINGS

FIG. 1 is an illustration of the flowering plant of the new variety of miniature rose; and FIG. 2 is an illustration showing details of the new miniature rose variety.

DESCRIPTION OF PREFERRED EMBODIMENT

The following is a detailed description of my new variety, with color terminology in accordance with The Royal Horticultural Society Color Chart (R.H.S.C.C.) and horticultural terminology in accordance with standard terminology used in UPOV-approved horticultural guidelines. The terminology used in color descriptions herein refers to plate numbers in the aforementioned color chart unless otherwise indicated.

Parentage:

*Seed parent.*—Unnamed seedling.

*Pollen parent.*—Unnamed seedling.

Class: Miniature.

As can be seen in the accompanying illustrations, FIG. 1 shows one sample of flowering plant of "Ruifaro" depicting the pot plant habit of growth and flowering. Since flowering is nearly continuous, the floriferous "Ruifaro" pot plant can remain attractively in bloom for long periods when given proper care and culture. It may also be grown outdoor in gardens.

FIG. 2 shows details of the new variety "Ruifaro". In the illustration there is shown the top of a young shoot, 1; compound three, five and seven leaflet leaves, 2, 3, and 4, respectively; a flower stem, 5; flower buds, 6 as sepals begin to separate, and, 7, after petals begin to unfurl; a flower, 8, about one-third to one-half open; and a bloom, 9, fully open. Also shown are flower stems 10, 11, and 12, displaying reproductive organs.

The following further horticultural observations were made of specimens grown outdoor in Holland.

FLOWER

Blooming habit: Nearly continuous.

A. Bud:

(1) *Size.*—Medium.

(2) *Form.*—Pointed, ovate.

(3) *Color.*—As sepals begin to separate, bud color is near 63B. After sepals part bud color is near 63B to D. Outer petals are imbued with light yellow-off white underlay toward point of petal attachment.

(4) *Sepals.*—Longer than bud, simple to foliated.

(5) *Penduncle.*—Length — 3 to 5 cm. Aspect — straight. Strength — erect. Color — medium green.

B. Bloom:

*Flower.*—Average size for miniature; viewed from top — rounded; viewed from side: (A) upper part of fully opened flower — flattened convex; (B) lower part of fully opened flower — convex.

(1) *Size.*—Average size when fully expanded — about 4 to 5 cm.

(2) *Borne.*—Primarily, singly, one to a stem.

(3) *Form.*—Ovoid at first, becoming flat then convex at maturity, outer petals reflex to point, inner petals roll under.

(4) *Petalage.*—Number of petals under normal conditions — many about 24 to 30, fully double.

(5) *Color.*—After sepals fall and petals unfurl, predominant flower color is light pink near 63B to 63D (HCC 25/2 to 25/1) with deeper hues where petals bunch. Color is substantially stable but with some lightening of margins of outer petals. As blooms mature, flower coloring tends to lighten, especially at outer petals. On reverse, petals are lighter toned and may be imbued with light colored underlay toward point of petal attachment approaching near 1D. Overall tonality from a distance is an attractive medium pink.

(6) *Flowering.*—Medium number of flowers.

C. Petals:

(1) *Texture.*—Medium to thick.

(2) *Appearance.*—Inside velvety and outside satiny.

(3) *Form and size.*—Broad obovate, little or no undulation at margin.

(4) *Arrangement.*—Regularly arranged, imbricated.

(5) *Petaloids in center.*—Several.

(6) *Persistence.*—Drop off cleanly.

(7) *Fragrance.*—Slight to none.

(8) *Lasting quality.*—Long lasting quality on plant.

REPRODUCTIVE ORGANS

A. Stamens, filaments and anthers:

*Arrangement and color.*—Regularly arranged around styles; color — filaments yellow green.

B. Pollen:

*Color.*—Yellow.

C. Styles: Long, pale green, little or no hairiness in upper half.

D. Stigma: Full, above anthers.

E. Hips: Small, funnel-shaped.

PLANT

A. Form: Upright to bushy.

B. Growth: Vigorous.

*Height attained.*—About 20 to 30 cm.

C. Foliage: Compound 3, 5 and 7 leaflets.

(1) *Size.*—Medium for a miniature.

(2) *Quantity.*—Abundant.

(3) *Color.*—Foliage at time of first flowering — medium green.

(4) *Shape.*—Oval, pointed.

(5) *Texture.*—Upper side is weakly glossy; under side is matte.

(6) *Edge.*—Serrate.

(7) *Serration.*—Ordinary, acuminate apices.

(8) *Leaf stem.*—Color — medium green.

(9) *Stipules.*—Medium length, slightly bearded, light green, distinct auricle.

(10) *Leaflet.*—Cross section — slight convex. Terminal leaflet — length of blade, very short; maximum width, very narrow; shape of base, rounded, weak undulation at margin; petiole length short.

D. Wood:

(1) *New wood.*—Color — purple.

(2) *Old wood.*—Color — medium green.

E. Prickles (thorns):

(1) *Prickles.*—Present, quantity (main stalk) few to ordinary; on laterals from stalk — ordinary; form — straight and slanted downward shape of upper side — flat; shape of lower side — concave; number of short prickles ($\leqq 5$ mm) — medium; number of long prickles ($>5$ mm) — very few; color — tan; position — irregular.

F. Winter hardiness: Needs protection outdoors in severe climates.

I claim:

1. A new and distinct variety of rose plant of the miniature rose class, substantially as shown and described, characterized particularly by a plant suitable for growing in pots and outdoor in gardens and by attractive medium pink flowers which are long lasting on the plant.

* * * * *

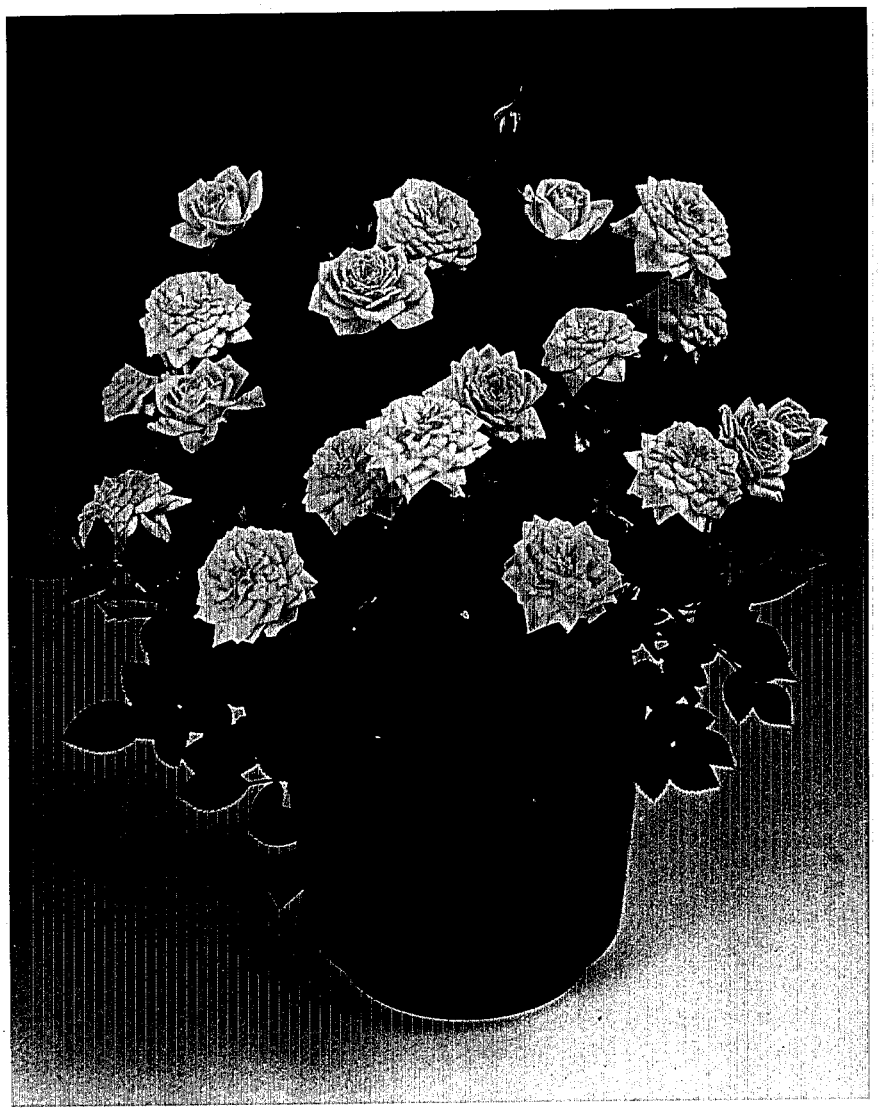

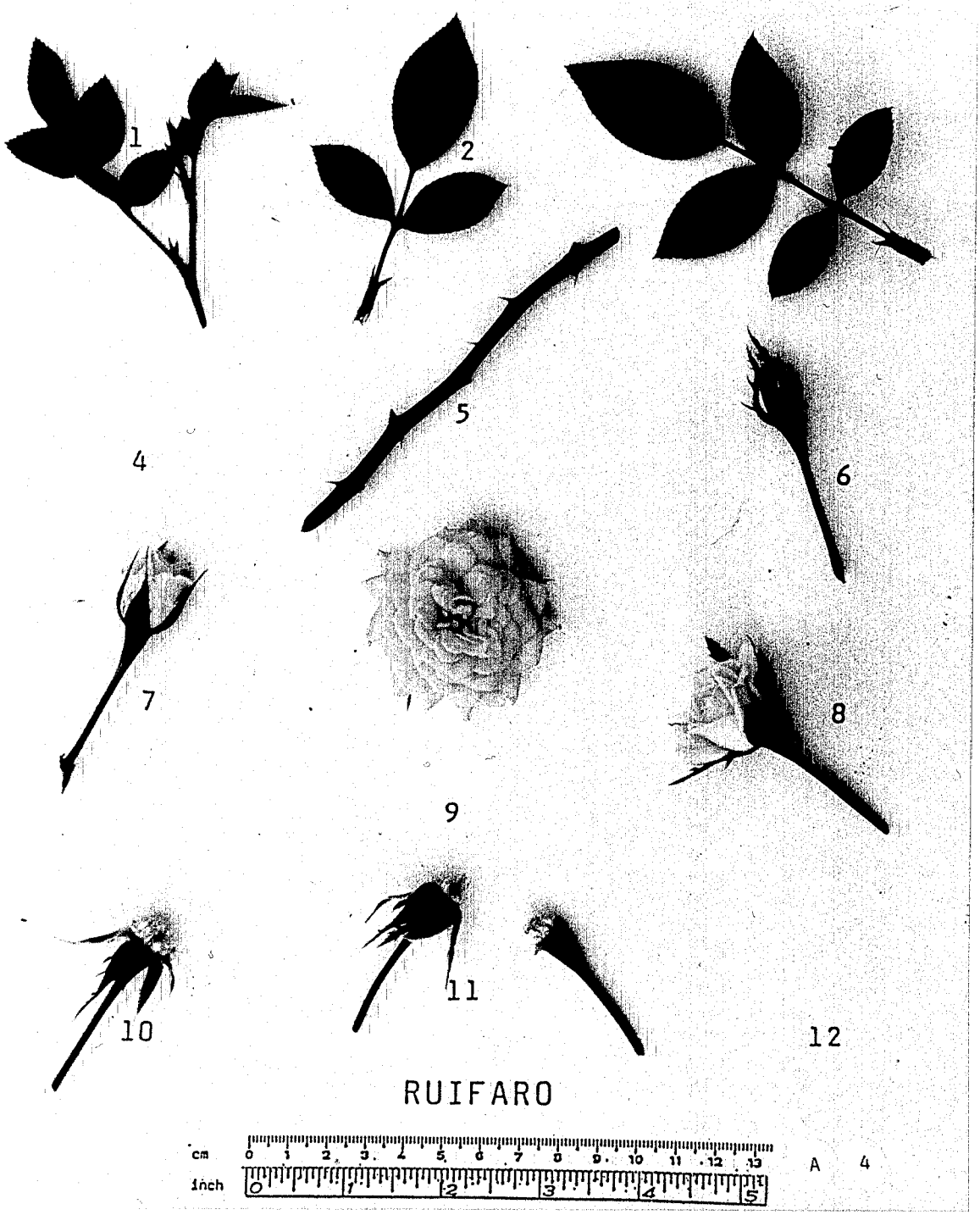
1
2
4
5
6
7
8
9
10
11
12
RUIFARO
cm
inch
A 4